US012376765B2

(12) United States Patent
Demircan et al.

(10) Patent No.: US 12,376,765 B2
(45) Date of Patent: Aug. 5, 2025

(54) MOVEMENT ANALYSIS AND FEEDBACK SYSTEMS, APPLICATIONS, DEVICES, AND METHODS OF PRODUCTION THEREOF

(71) Applicant: The Trustees of the California State University, Long Beach, CA (US)

(72) Inventors: Emel Demircan, Long Beach, CA (US); I-Hung Khoo, Irvine, CA (US); Elliot Recinos, West Covina, CA (US)

(73) Assignee: The Trustees of the California State University, Long Beach, CA (US)

( * ) Notice: Subject to any disclaimer, the term of this patent is extended or adjusted under 35 U.S.C. 154(b) by 151 days.

(21) Appl. No.: 18/115,198

(22) Filed: Feb. 28, 2023

(65) Prior Publication Data

US 2023/0277092 A1 Sep. 7, 2023

Related U.S. Application Data

(63) Continuation of application No. 16/995,566, filed on Aug. 17, 2020, now Pat. No. 11,589,782.

(51) Int. Cl.
*A61B 5/00* (2006.01)
*A61B 5/11* (2006.01)

(52) U.S. Cl.
CPC ............ *A61B 5/112* (2013.01); *A61B 5/0004* (2013.01); *A61B 5/0015* (2013.01); *A61B 5/6804* (2013.01); *A61B 5/7405* (2013.01); *A61B 5/742* (2013.01); *A61B 5/7455* (2013.01); *A61B 2562/0219* (2013.01)

(58) Field of Classification Search
CPC ..... A61B 5/112; A61B 5/0004; A61B 5/0015; A61B 5/6804; A61B 5/7405; A61B 5/742; A61B 5/7455; A61B 2562/0219; A61B 5/7275; A61B 5/1121; A61B 5/389; A61B 5/4585; A61B 5/6803; A61B 5/6807; A61B 5/6823; A61B 5/6824; A61B 5/6828; A61B 5/7435; A61B 5/744; A61B 5/0024; G16H 15/00; G16H 20/30; G16H 50/50; G16H 40/63; G16H 50/30
See application file for complete search history.

(56) References Cited

U.S. PATENT DOCUMENTS

| | | | |
|---|---|---|---|
| 11,112,868 B1 * | 9/2021 | Stewart | G06F 3/016 |
| 11,179,066 B2 * | 11/2021 | Kaifosh | A61B 5/0077 |
| 11,231,745 B1 * | 1/2022 | Momcilovic | A63F 13/212 |
| 11,285,032 B2 * | 3/2022 | Eugene | A41B 11/003 |
| 11,337,652 B2 * | 5/2022 | Kaifosh | G06V 10/764 |

(Continued)

FOREIGN PATENT DOCUMENTS

WO    WO-2015164456 A2 *    10/2015    ........... A43B 3/0015

*Primary Examiner* — May A Abouelela
(74) *Attorney, Agent, or Firm* — Sandra Thompson; Finlayson Toffer

(57) ABSTRACT

Contemplated systems for monitoring and analysis of human motion synthesis are disclosed herein that include: at least one garment configured to be worn by a user, at least one inertial sensor, wherein the at least one inertial sensor is integrated with or into the at least one garment, an information system, wherein the information system communicates with the at least one inertial sensor to produce a set of data, at least one musculorientation metric generated by the information system, and at least one performance report that is produced from the analysis of the at least one musculorientation metric.

11 Claims, 5 Drawing Sheets

(56) References Cited

U.S. PATENT DOCUMENTS

| | | | | |
|---|---|---|---|---|
| 2015/0366504 | A1* | 12/2015 | Connor | A61B 5/6804 |
| | | | | 600/301 |
| 2016/0198998 | A1* | 7/2016 | Rahimi | A61B 5/4519 |
| | | | | 600/595 |
| 2016/0338644 | A1* | 11/2016 | Connor | A61B 5/1126 |
| 2017/0156662 | A1* | 6/2017 | Goodall | A61N 2/002 |
| 2017/0196513 | A1* | 7/2017 | Longinotti-Buitoni | |
| | | | | D06P 1/5285 |
| 2017/0319132 | A1* | 11/2017 | Longinotti-Buitoni | |
| | | | | A61B 5/0002 |
| 2018/0008196 | A1* | 1/2018 | Connor | A61B 5/1126 |
| 2018/0140902 | A1* | 5/2018 | Wiebe | A61B 5/1118 |
| 2018/0242654 | A1* | 8/2018 | Marikkar | A61B 5/7455 |
| 2018/0307314 | A1* | 10/2018 | Connor | G06F 3/017 |
| 2019/0247650 | A1* | 8/2019 | Tran | A61N 1/3704 |
| 2019/0283247 | A1* | 9/2019 | Chang | A61B 5/1121 |
| 2019/0343459 | A1* | 11/2019 | Korzinov | A61B 5/316 |
| 2019/0344121 | A1* | 11/2019 | Wells | A61B 5/6805 |
| 2020/0163621 | A1* | 5/2020 | Connor | A61B 5/389 |
| 2020/0401224 | A1* | 12/2020 | Cotton | A61B 5/742 |
| 2021/0169326 | A1* | 6/2021 | Emokpae | A61B 5/0205 |
| 2021/0361165 | A1* | 11/2021 | Rogers | A61B 5/683 |
| 2022/0035443 | A1* | 2/2022 | Winold | G06V 20/20 |
| 2022/0054084 | A1* | 2/2022 | Chahine | A61B 5/11 |
| 2022/0244032 | A1* | 8/2022 | Connor | G06F 3/015 |

\* cited by examiner

MOVEMENT ANALYSIS AND FEEDBACK SYSTEMS, APPLICATIONS, DEVICES, AND METHODS OF PRODUCTION THEREOF

FIELD OF THE SUBJECT MATTER

The field of the subject matter is movement analysis and feedback systems, applications, devices, and methods of production of those systems, applications, and devices.

BACKGROUND

Movement is a basic feature of human existence and is intimately connected to quality of life. Movement training can prevent injury, improve athletic performance, delay musculoskeletal disease and accelerate rehabilitation. Until now, training has been limited in scope to specialized training facilities and limited in effectiveness to the verbal recommendations of physical trainers. We seek to expand the scope and effectiveness of human movement training to extend health and lifestyle benefits to the general public.

Since the 1970's, running popularity has continuously grown as a professional and recreational sport. It is estimated that 65 million people participated in this activity in United States alone in 2017 [statista.com]. Between 1990 and 2013, road race finishers grew from five million to over 19 million [runningusa.org]. Contributing to its popularity, running was proved to have major health benefits, such as improving cardiovascular endurance and overall quality of life, and decreasing the prevalence of type 2 diabetes, obesity, and hypertension [Kalak et al. 2012]. In the U.S., 10-20% of the population run regularly, with 40-50% injured annually [Jeannie et al., 2010]. Among these injuries, half occur at the knee joint, with patellofemoral pain (PFP) being the most common diagnosis [Taunton et al 2002, Totaro et al 2017]. PFP can lead to severe pain and disability and is a precursor of knee osteoarthritis [Thomas et al 2010]. There lies a huge potential for sports science and physical therapy to use feedback mechanisms as intervention tool [VenBreda et al 2017].

Arthritis is the leading cause of disability among adults in the U.S. Knee osteoarthritis is the most prevalent form of arthritis afflicting 28% of U.S. adults over age 45 and 37% of U.S. adults over age 65. $128 billion in total costs or 1.2% of the U.S. gross domestic product was spent on arthritis in 2003. Reducing the incidence of arthritis by even 1% would cut the total cost by $1.3 billion per year, a savings of more than $3.5 million per day [Lawrence et al 2008, Helmik et al 2008].

Knee joint osteoarthritis (OA) is a significant public health problem causing pain and limiting mobility and is believed to have mechanical etiology. Retraining one's walking gait can alter the loads placed on the knee, reducing the risk of developing OA and halting disease progression. The joint moment applied to the knee in the frontal plane during walking (knee adduction moment) has been linked to the development, progression, and severity of knee joint OA [Schipplein and Andriacchi 1991, Andriacchi 1994]. The knee adduction moment provides an estimate of the load placed on the medial compartment of the joint [Schipplein and Andriacchi 1991] and reducing the knee adduction moment offers a promising metric for preventing and treating medial compartment knee OA. Traditionally, exercise and physical therapy have been used to strengthen muscles surrounding affected joints [Ettinger et al 1997, Kovar et al 1992] in an attempt to reduce loads. Orthopaedic surgery has also focused on reducing the loads on the medial part of the knee. An example of this is a high tibial osteotomy (HTO), which has been shown to reduce the knee adduction moment by 30-35% [Visintin et al 1998, Prodromos et al 1985]. However, HTO is not effective in all cases and patients with large knee adduction moments prior to surgery sometimes maintain these high moments following surgery [Prodromos et al 1985].

Hip OA is correlated with loading patterns in the hip joint during ambulatory motion [Frost 1994, Radin 1991]. Many patients naturally alter gait to reduce hip pain from dysplasia [Schroter 1991] and OA [Hurwitzh 1997, Wall 1981]. It is therefore feasible that a patient's ambulation could be retrained to change biomechanical loads, slowing or halting the onset and progression of hip OA. Hip arthroplasty resulting from musculoskeletal disease often leads to gait asymmetry, which can be corrected through movement retraining. Today, the most effective forms of treating OA in the hip and the knee are through surgery or prolonged rehabilitation. These treatments are invasive, expensive and not guaranteed to work. Thus, hip OA, like knee OA, is in need of a new, inexpensive and effective motion retraining solution.

Many other neurological disorders would benefit from novel and effective movement analysis and retraining strategies. Children with cerebral palsy, for example, benefit from muscle strength training [Dodd 2002], lower limb orthoses [Morris 2002] and functional electrical stimulation [Kerr 2004]. Other movement-impaired neurological disorders which would benefit from a more efficient and effective form of movement retraining include spinal cord injury [Barbeau 1999, Wirz 2005, Behrman 2000], traumatic brain injury [Khan 2003, Gordon 2006] and Parkinson's disease [Morris 2001, Gage 2004].

There has been much research in developing smart wear with integrated sensors, with applications in different areas. Some recent examples that involve soft suits which can be used in daily activities. The commercial product by Athos, which was described in U.S. patent Ser. No. 10/292,652, includes a compression shirt and shorts with integrated inertial measurement unit (IMU) and electromyography (EMG) sensors, both of which are biometric sensors. It provides visual information on muscle efforts using a smartphone app (www.liveathos.com).

There are several deficiencies in the Athos design, however. First, the soft suits are only designed to provide simple muscle-based metrics from the muscle activity of the user. For those wearers who are looking for a more comprehensive feedback and analysis system, the Athos design will not provide that system. Second, the sensors used in the Athos design are biometric sensors, which leads to the relatively superficial nature of the feedback and analysis. Third, the Athos design is not designed to provide real-time feedback and analysis during the activity of the wearer. The feedback provided by the Athos system is after the activity is completed. While this provides some useful information to the wearer, it does not help the wearer retrain his or her movement during the activity itself.

Contemplated objectives should include to develop a cyber-physical system that uses sensed information along with computer models of human locomotion to characterize an individual's running gait and that provides multi-modal feedback signals for gait training to close the loop and improve human motion over time. Analyzing human running through modeling and algorithmic tools from both robotics and biomechanics increases our scientific understanding of gait mechanics and control, and the resulting models also provide a basis for clinicians to quantify characteristics of a subject's gait and to design effective treatments, like gait retraining or muscle strengthening. Improved ability to identify and correct risky running behaviors would have broad impact, as over 10% of Americans run regularly, with over half estimated to suffer running-related injuries annually (Jeannie et al., 2010). On the other hand, knee osteoarthritis is the most prevalent form of arthritis afflicting 28% of U.S. adults over age 45 and 37% of U.S. adults over age 65. Reducing the incidence of arthritis by even 1% would cut the total cost by $1.3 billion per year, a savings of more than $3.5 million per day.

SUMMARY OF THE SUBJECT MATTER

Contemplated systems for monitoring and analysis of human motion synthesis are disclosed herein that include: at least one garment configured to be worn by a user, at least one inertial sensor, wherein the at least one inertial sensor is integrated with or into the at least one garment, an information system, wherein the information system communicates with the at least one inertial sensor to produce a set of data, at least one musculorientation metric generated by the information system, and at least one performance report that is produced from the analysis of the at least one musculorientation metric.

Other contemplated systems for monitoring and analysis of human motion synthesis are disclosed herein that include: at least one garment configured to be worn by a user, at least one inertial sensor, wherein the at least one inertial sensor is integrated with or into the at least one garment, an information system, wherein the information system communicates with the at least one inertial sensor to produce a set of data, at least one musculorientation metric generated by the information system, and at least one performance report that is produced from the analysis of the at least one musculorientation metric, wherein the at least one performance report is generated during the user's motion, immediately after the user's motion, or a combination thereof.

Yet other contemplated systems for monitoring and analysis of human motion synthesis are disclosed herein that include: at least one garment configured to be worn by a user, at least one inertial sensor, wherein the at least one inertial sensor is integrated with or into the at least one garment, an information system, wherein the information system communicates with the at least one inertial sensor to produce a set of data, at least one musculorientation metric generated by the information system, and at least one performance report that is produced from the analysis of the at least one musculorientation metric, wherein the at least one performance report is generated as concurrent feedback via haptics information, is generated as terminal feedback via visual information, or a combination thereof.

Another contemplated software system that analyzes human motion synthesis is disclosed herein that comprises: a two-way communications system, an information system, wherein the information system communicates with at least one inertial sensor through the two-way communications system, wherein the at least one inertial sensor is integrated with or into at least one garment to produce a set of data, at least one musculorientation metric generated by the information system, and at least one performance report that is produced from the analysis of the at least one musculorientation metric.

DETAILED DESCRIPTION

The wearable technology market is expected to witness high growth. The overall wearable technology market is expected to grow from USD 15.7 billion in 2015 to USD 51.6 billion by 2022, at a CAGR of 15.51% from 2016 to 2022. Application areas range from consumer durables and healthcare to enterprise, research and so on. Target customers include sportsman (i.e. runners), university/varsity teams, fitness/training centers, rehabilitation facilities, research institutions/universities (i.e. robotics/biomechanics labs, departments including kinesiology, physical therapy, engineering) and end users who want to know more about the wearable technology and the latest technological developments in this industry. Market drivers are consumer preference for sophisticated gadgets, increasing growth prospects of next generation displays in wearable devices, and growing popularity of Internet of Things (IoT) and connected devices. Market opportunities include adoption of wearables in multiple application areas, and multi-featured and hybrid application mobile devices.

Figure 1:
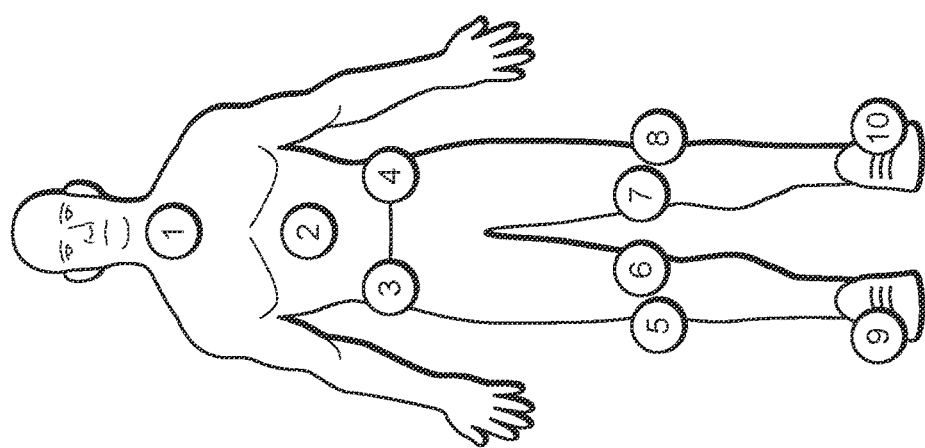
FIG. 1 shows contemplated locations of the vibrotactile or inertial motors or sensors.

In general, a system for human motion synthesis and analysis is contemplated herein, which comprises integrated inertial measurement units to track the motion and orientation of the body and limb segments. FIG. 1 shows contemplated locations for vibrotactile motors or inertial sensors 1-10. There may be additional inertial sensors located throughout contemplated systems, as needed.

Contemplated software/framework reconstructs an anatomically accurate musculoskeletal system that is scaled to represent the subject, along with analysis of the musculoskeletal system with respect to the movement of the user, and presentation of performance reports and metrics. The musculoskeletal system is used for synthesis and analysis of the motion to improve the performance metrics. The musculoskeletal system comprises the skeletal bone system geometry, muscle system, and degree of freedoms of body joints. The anatomically accurate musculoskeletal system is driven by the motion and orientation of the body and limb segments tracked.

Contemplated movement analysis and feedback systems use sensed information along with computer models of human locomotion to characterize an individual's running gait and that provides multi-modal feedback signals for gait training to close the loop and improve human motion over time. Analyzing human running through modeling and algorithmic tools from both robotics and biomechanics increases our scientific understanding of gait mechanics and control, and the resulting models also provide a basis for clinicians to quantify characteristics of a subject's gait and to design effective treatments, like gait retraining or muscle strengthening.

Specifically, contemplated systems for monitoring and analysis of human motion synthesis are disclosed herein that include: at least one garment configured to be worn by a user, at least one inertial sensor, wherein the at least one inertial sensor is integrated with or into the at least one garment, an information system, wherein the information system communicates with the at least one inertial sensor to produce a set of data, at least one musculorientation metric generated by the information system, and at least one performance report that is produced from the analysis of the at least one musculorientation metric. In contemplated embodiments, the set of data comprises the user's motion data.

Other contemplated systems for monitoring and analysis of human motion synthesis are disclosed herein that include: at least one garment configured to be worn by a user, at least one inertial sensor, wherein the at least one inertial sensor is integrated with or into the at least one garment, an information system, wherein the information system communicates with the at least one inertial sensor to produce a set of data, at least one musculorientation metric generated by the information system, and at least one performance report that is produced from the analysis of the at least one musculorientation metric, wherein the at least one performance report is generated during the user's motion, immediately after the user's motion, or a combination thereof. As contemplated and as will be described herein, the at least one performance report is generated as concurrent feedback via haptics information, including vibrotactile or other haptic modalities, as audio information; is generated as terminal feedback via visual information; or a combination thereof.

Figure 2:
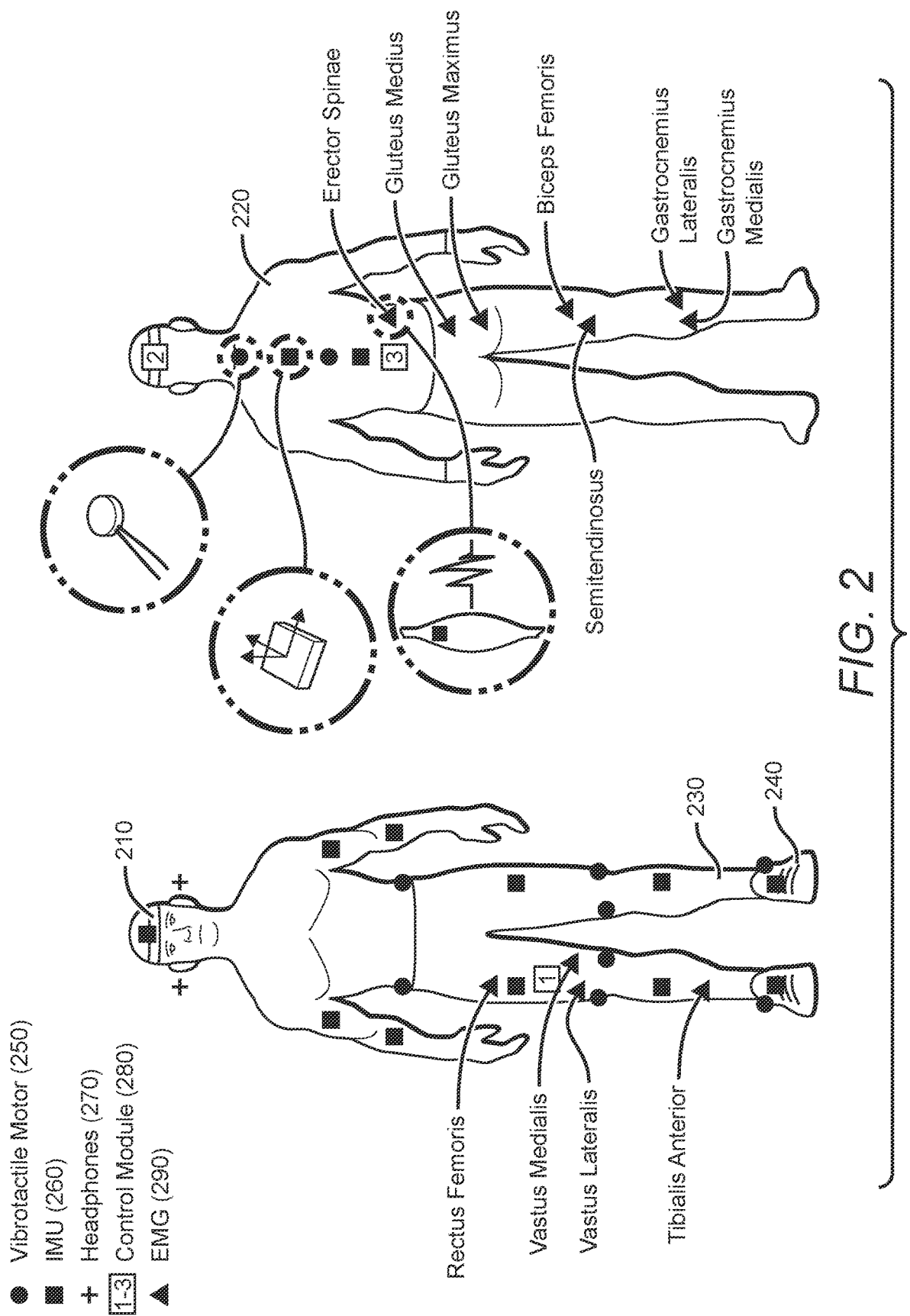
FIG. 2 shows a contemplated CyberSuit and its Sensory/Feedback Hardware Components.

Contemplated garments comprise four main components: a headband 210, a shirt 220, a pair of pants 230, and shoelaces 240, or a combination thereof, which is shown in FIG. 2. Additional embodiments may include a jacket or shorts. Each of these components have non-biometric sensors to measure motion and measure muscle activities. In FIG. 2, the positions of vibrotactile motors 250 and inertial sensors 260 are shown, along with IMUs, headphones 270, control modules 280, and EMGs 290. Haptic feedback is provided by motors or sensors embedded in the suit. The headband includes a microphone to receive the subject's inputs, such as his/her comfort, during training. The tactile motors are placed on strategic locations on the body for effective tactile feedback, which is included in the at least one performance report that is generated during the user's motion. The performance of various types of motors have been evaluated in preliminary testing and promising results have been observed using eccentric-mass motors with proper orientation to focus the vibration direction perpendicular to the skin surface. The suit includes the main control module which serves as the central processing unit to process the sensor data, model the dynamics, and decide on which feedback to activate.

Contemplated systems include at least one inertial sensor, wherein the at least one inertial sensor is integrated with or into the at least one garment. Contemplated primary inertial sensors are non-biometric sensors. An EMG sensor, for example, is a biometric sensor and therefore it is not contemplated herein as the sole source or even the primary source of data. At least one EMG sensor could be used as a secondary source of information for contemplated systems, but again, it is not a primary source of data.

It should be understood that one primary goal of contemplated embodiments is the reconstruction of anatomical musculoskeletal system that is scaled to represent the subject for synthesis and analysis. Contemplated musculoskeletal systems include skeletal bone system geometry, muscle system, and degree of freedoms of body joints. Contemplated embodiments are driven by the tracking of the motion and orientation of the body and of the limb segments.

Contemplated systems also include an information system, wherein the information system communicates with the at least one inertial sensor to produce a set of data. Contemplated information systems comprise a main control module and at least one additional control module. Contemplated information systems are designed to wirelessly communicate with the at least one inertial sensor. In some embodiments, the communications path is a one-way path from the inertial sensors to the information system. In other embodiments, the communications path is a two-way path from the inertial sensors to the information system and then back in the other direction, as the information system works with and/or adjusts the sensors to gather additional information and data. In some embodiments, the communication from the information system back to the at least one inertial sensor comprises at least one feedback instruction.

In contemplated systems, at least one musculorientation metric is generated by the information system. As defined herein, a "musculorientation metric" means a metric or data point that is the numerical result of tracking at least some part of the motion, orientation, or a combination thereof of a body segment, a limb segment, or a combination thereof. The musculorientation metrics are those metrics that are used to produce the at least one performance report for the wearer and/or user. As part of the performance report, a contemplated analysis can review and provide information on trunk and/or body lean, pelvic tilt, knee movement and/or moment, foot strike pattern, ground reaction force, fatigue, along with other suitable performance metrics. In some embodiments, at least one performance report is generated instantaneously for the user. In other embodiments, at least one performance report is generated as concurrent feedback via haptics information, is generated as terminal feedback via visual information, or a combination thereof. In yet other embodiments, the at least one performance report is generated during the user's motion, immediately after the user's motion, or a combination thereof.

Figure 3:
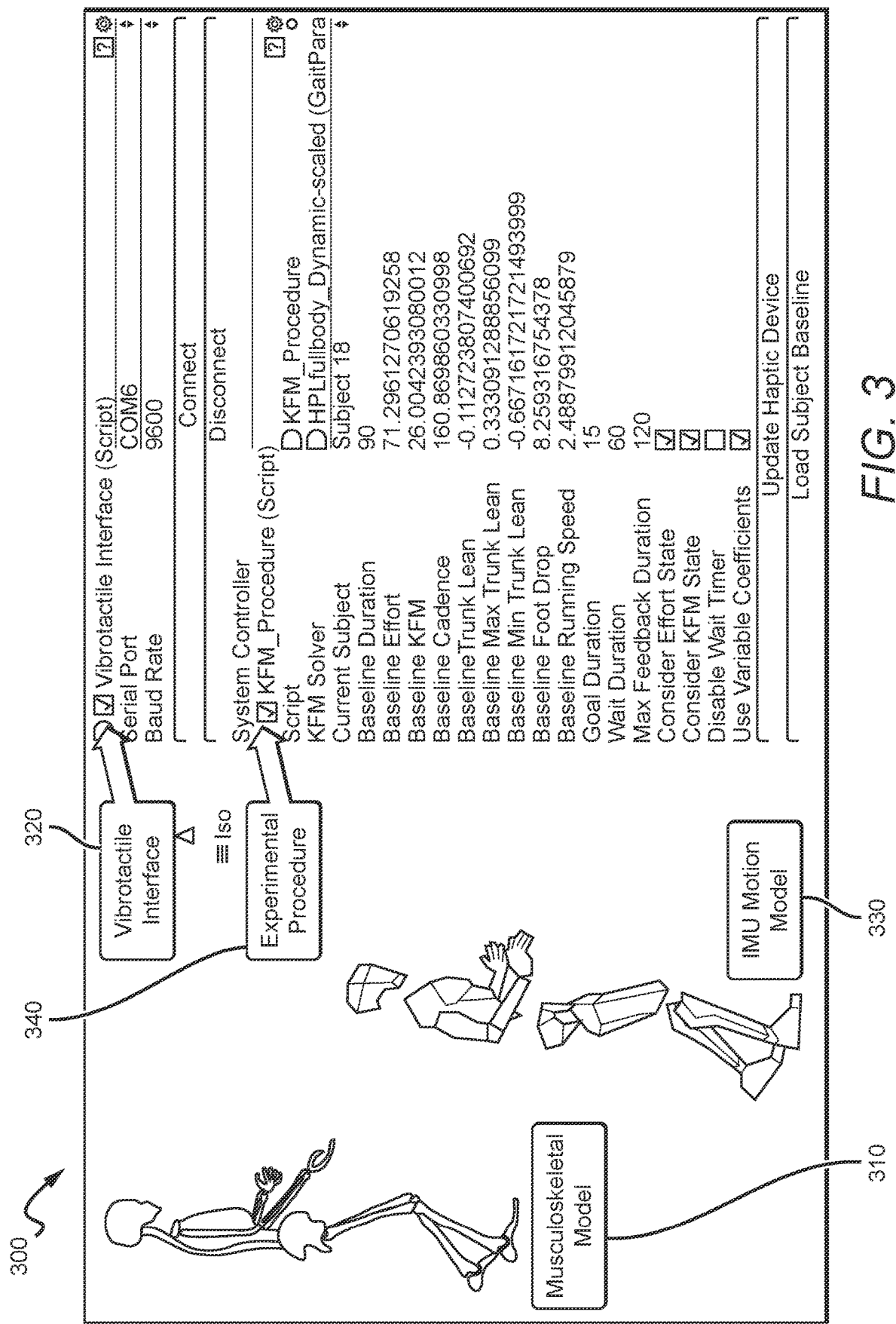
FIG. 3 shows a contemplated simulation framework.

It should be understood that the at least on performance report will include or incorporate complex calculations in real-time handle by low-power custom circuits employing parallel computing paradigm locally on the system. In many contemplated embodiments, calculations are performed locally and not remotely on a cloud or remote server, which is why contemplated systems are able to provide information in real-time for the wearer. FIG. 3 shows a contemplated user interface that provides a performance report 300 for the user, wherein a musculoskeletal model 310 is coupled with a vibrotactile or inertial interface 320, an IMU motion model 330, and an experimental procedure script 340 that is part of the system controller system. It should be understood that the design of this user interface and performance report can take a number of different representations and can include more or less information, depending on the system The system shown in FIG. 3 is an example, but other systems are contemplated.

There are some potential challenges to systems contemplated herein, including battery life and cost. These challenges can be overcome in a number of ways, including developing in-house non-biometric sensors and integrating those with the haptic suit. As smaller and more powerful non-biometric sensors are developed commercially, those can be integrated easily into this technology at a lesser cost. In addition, the performance of various types of motors have been evaluated in preliminary testing, as shown in Example 1, and promising results have been observed using eccentric-mass and low-cost motors with proper orientation to focus the direction perpendicular to the skin surface.

The IMU is a compact sensor frequently used in wearables to detect orientation. However, one issue is that its readings drift over time, which affects the accuracy of the measured orientation. In low cost MEMS IMUs, sensor fusion algorithms are commonly used to compensate for the drift. Contemplated devices will further reduce the drift by utilizing a hybrid IMU design with custom algorithm. Contemplated devices also include on-the-fly calibration, as well as error zeroing during periods of inactivity. This new low-drift IMU will allow the haptic suit to be used continuously during a typical training session.

Contemplated kinematic and dynamic modeling in real-time requires a lot of computing power. Most micro-controllers do not have the computational speed required. A regular microprocessor, although fast, dissipates too much power and heat to be used in a wearable. Contemplated designs for the processing unit for the haptic suit will utilize a unique combination of micro-controllers with a custom circuit such as a field-programmable-gate-array (FPGA) or application-specific-integrated-circuit (ASIC). A contemplated micro-controller will perform the general computation while the FPGA/ASIC will handle the complex kinematic calculation and modeling.

With this hybrid approach, the high speed and low power requirements can be met in the system. Software and hardware systems that are designed to implement and complete contemplated kinematic modeling and inertial analysis are contemplated herein.

A contemplated software system that analyzes human motion synthesis is disclosed herein that comprises: a two-way communications system, an information system, wherein the information system communicates with at least one inertial sensor through the two-way communications system, wherein the at least one inertial sensor is integrated with or into at least one garment to produce a set of data, at least one musculorientation metric generated by the information system, and at least one performance report that is produced from the analysis of the at least one musculorientation metric. In some contemplated embodiments, the two-way communications system comprises at least one wireless link.

EXAMPLES

Example 1

Figure 5:
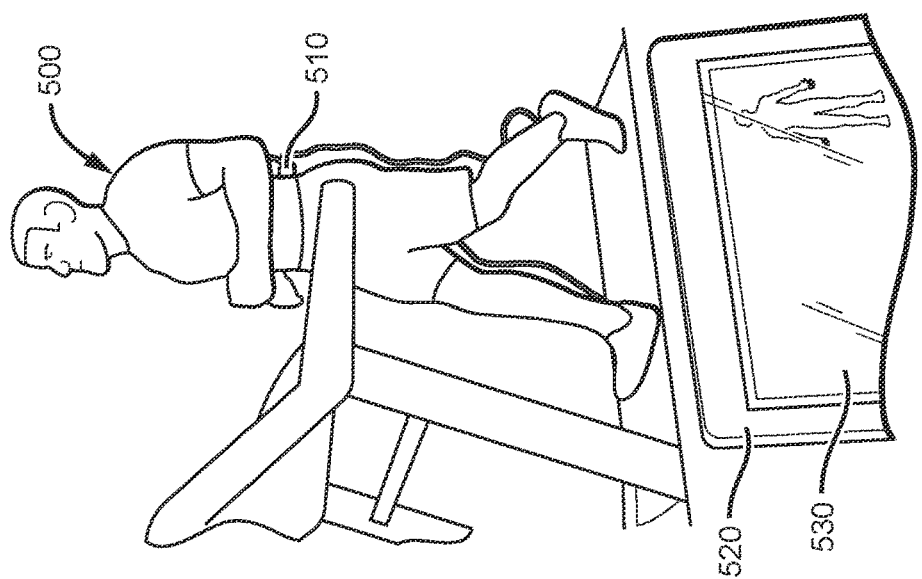
FIG. 5 shows a contemplated experimental setup and system Graphical User Interface (GUI).
Figure 4:
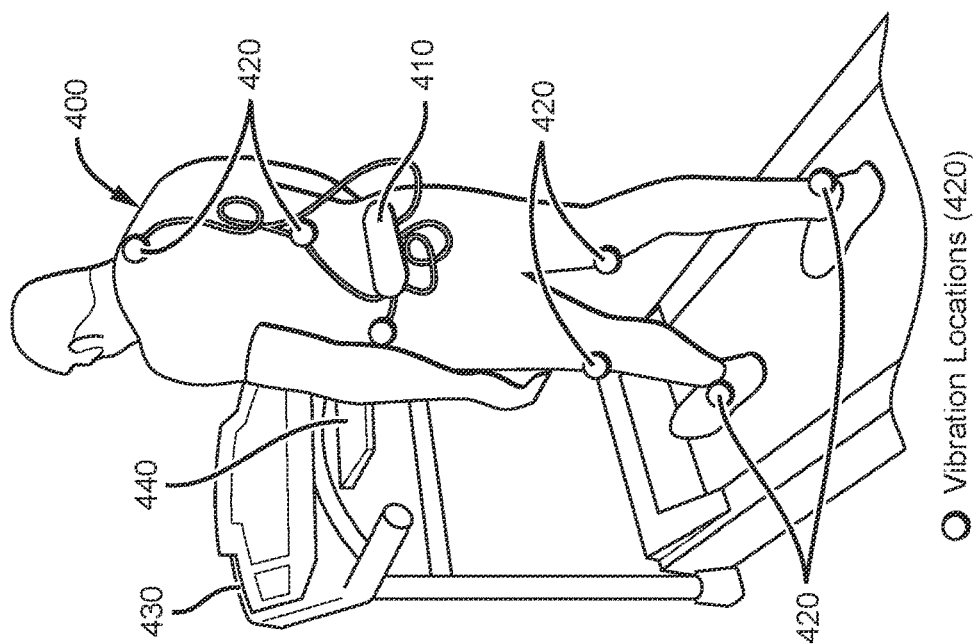
FIG. 4 shows an example of a subject wearing the wireless sensing and feedback system.
Figure 7:
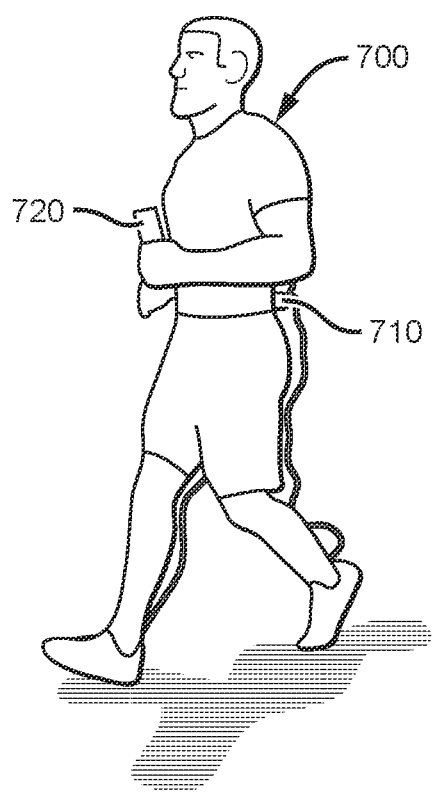
FIG. 7 shows the same user 700 with the graphical user interface 720 or GUI, which in this contemplated embodiment is the smart phone that the user is carrying, that is gathering the data from the haptic feedback hardware 710 and providing the at least one performance report (not shown in this Figure).

FIG. 4 shows a contemplated user 400 wearing a contemplated system that includes haptic feedback hardware 410, and a plurality of vibration locations 420. In this embodiment, the user is on a treadmill 430 with a button/operation panel 440. FIG. 5 shows the same user 500 with the graphical user interface 520 or GUI that is gathering the data from the haptic feedback hardware 510 and providing the at least one performance report 530. FIG. 7 shows the same user 700 with the graphical user interface 720 or GUI, which in this contemplated embodiment is the smart phone that the user is carrying, that is gathering the data from the haptic feedback hardware 710 and providing the at least one performance report (not shown in this Figure). It should be understood that the treadmill is used as a way to provide an efficient way for the user to move; however, the treadmill is not necessary, if the user is able to walk outside or on an indoor/outdoor track.

Table 1 shows the motors comparison when comparing conventional systems with the novel design disclosed herein. The last row of the table illustrates the novel design, which was based on the benchmark. The study found that the novel design was more cost effective, lightweight, and better in performance than conventional designs.

|  | Acceleration peak-to-peak (G) | | | Vibration magnitude (G) (normalized wrt 100 g test sled) | Weight (g) |
| --- | --- | --- | --- | --- | --- |
|  | X | Y | Z | | |
| Conventional A | 0.20 | 0.34 | 4.77 | 3.01 | 17.00 |
| Conventional B | 0.51 | 0.45 | 2.39 | 1.26 | 8.00 |
| Conventional C | 2.96 | 0.65 | 2.58 | 1.99 | 5.00 |
| Conventional D | 0.75 | 1.08 | 3.76 | 1.63 | 0.95 |
| Conventional E | 1.77 | 1.26 | 0.22 | 0.89 | 1.00 |
| Conventional F | 1.75 | 1.16 | 0.34 | 0.87 | 0.80 |
| Contemplated Design | 4.55 | 0.84 | 4.01 | 2.76 | 4.00 |

Figure 6:
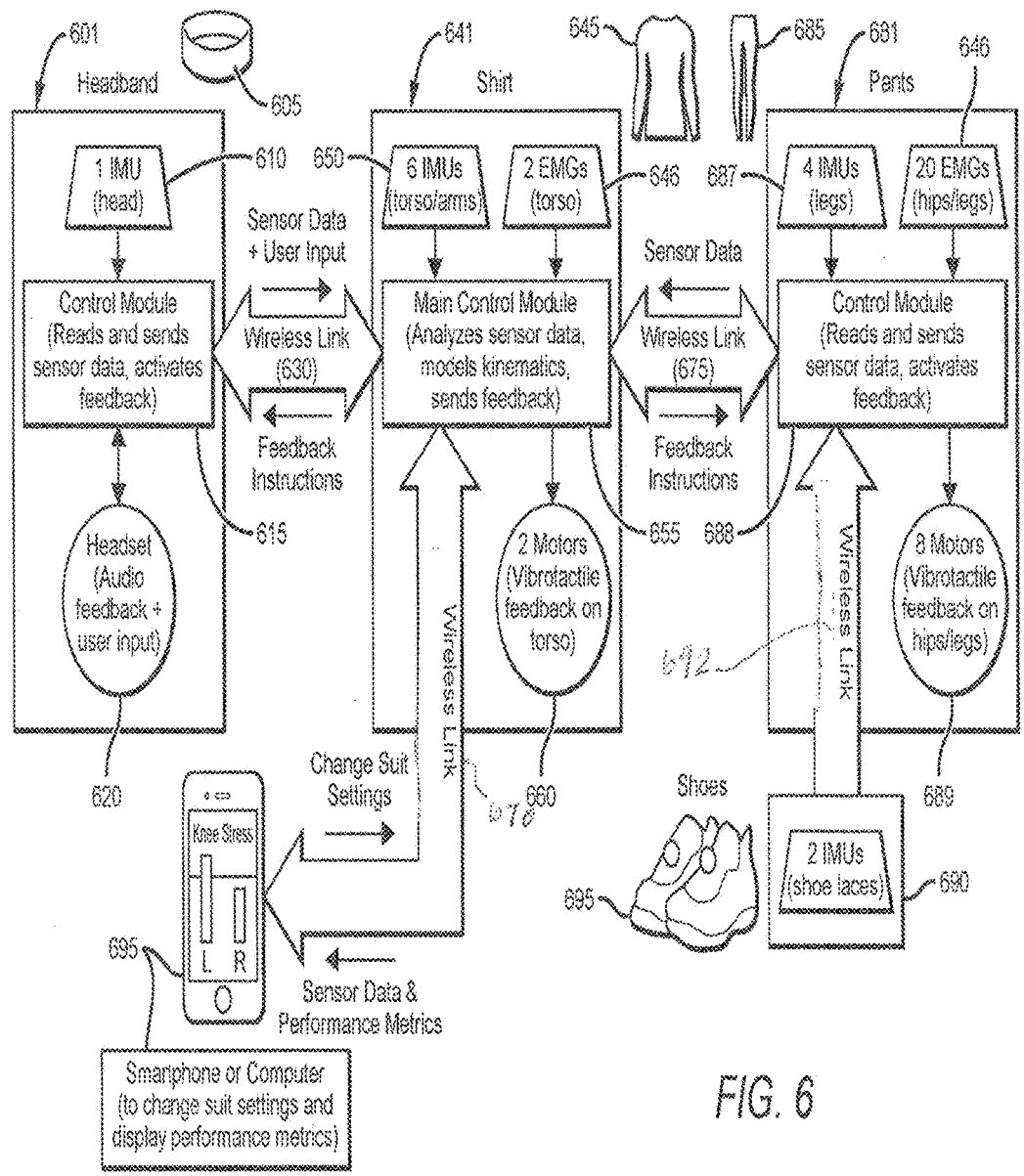
FIG. 6 shows a contemplated overview of the CyberSuit Software Components.

FIG. 6 shows a flow chart of how these different components of contemplated systems and how they may relate to one another. Block 601 shows the headband 605 and its contemplated constituents: an IMU 610, a control module 615, and at least one headset 620. A wireless link 630 communicatively connects the headband 605 and the shirt 645 in block 641. Shirt 645 comprises at least one IMU 650, a main control module 655, and at least one motor 660. In addition, there are two additional wireless links 670 and 675 that communicatively connects the shirt 645 with the smartphone or computer 695 and the pants 685 shown in block 681. Pants 685 comprises at least one IMU 687, at least one control module 688, and at least one motor 689. A wireless link 692 communicatively connects the pants 685 and the shoes 695 in block 690. There may also be a plurality of EMGs 646 on these components and are shown as part of the shirt 645 and the pants 685 in this Figure. It should be understood that the contemplated wireless links disclosed herein may be one-way communication links but are likely two-way communication links between the control modules and the main control module, which communicates with the smartphone or computer.

Thus, specific embodiments, methods of movement analysis and feedback systems have been disclosed. It should be apparent, however, to those skilled in the art that many more modifications besides those already described are possible without departing from the inventive concepts herein. The inventive subject matter, therefore, is not to be restricted except in the spirit of the disclosure herein. Moreover, in interpreting the specification and claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

We claim:

1. A system for monitoring and analysis of human motion synthesis, comprising:
   at least one garment configured to be worn by a user, at least one inertial sensor, wherein the at least one inertial sensor is integrated with or into the at least one garment, at least one electromyography sensor, wherein the at least one electromyography sensor is integrated with or into the at least one garment, a two-way communications system, wherein the two-way communications system comprises at least one wireless link, an information system, wherein the information system communicates with the at least one inertial sensor through the two-way communications system, and the at least one electromyography sensor to produce a set of data, at least one musculorientation metric generated by the information system, and at least one performance report that is produced from an analysis of the at least one musculorientation metric, wherein the at least one performance report includes a musculoskeletal model, a vibrotactile or inertial interface, an IMU motion model, and an experimental procedure script.

2. The system of claim 1, wherein the at least one garment comprises a shirt, a pair of pants, a pair of shorts, a jacket, a headband, a shoelace, or a combination thereof.

3. The system of claim 1, wherein the set of data comprises the user's motion data.

4. The system of claim 1, wherein the information system is a two-way communication circuit from the at least one inertial sensor to the information system and back to the at least one inertial sensor.

5. The system of claim 1, wherein the communicating from the information system back to the at least one inertial sensor comprises at least one feedback instruction.

6. The system of claim 1, wherein the at least one performance report is generated instantaneously for the user.

7. The system of claim 1, wherein the at least one performance report is generated as concurrent feedback via haptics information.

8. The system of claim 1, wherein the at least one inertial sensor comprises at least one non-biometric sensor.

9. The system of claim 1, wherein the at least musculorientation metric comprises at least one piece of information about a motion, an orientation, or a combination thereof of a body segment, a muscle segment, a limb segment, or a combination thereof.

10. The system of claim 1, wherein the at least one performance report is generated during the user's motion, immediately after the user's motion, or a combination thereof.

11. The system of claim 1, wherein the information system comprises a main control module and at least one additional control module.

* * * * *